(12) United States Patent
Gillick et al.

(10) Patent No.: US 6,383,206 B1
(45) Date of Patent: May 7, 2002

(54) EMBOLIC PROTECTION SYSTEM AND METHOD INCLUDING FILTERING ELEMENTS

(75) Inventors: Matthew J. Gillick; Scott J. Huter, both of Temecula; Kent C. B. Stalker, San Marcos; Benjamin C. Huter, Temecula; Anuja Patel, San Jose, all of CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/475,599

(22) Filed: Dec. 30, 1999

(51) Int. Cl.⁷ ............................................. A61M 29/00
(52) U.S. Cl. ................................... 606/200; 606/114
(58) Field of Search ................................ 606/200, 114, 606/127, 191, 1

(56) References Cited

U.S. PATENT DOCUMENTS

| | | | |
|---|---|---|---|
| 4,425,908 A | * | 1/1984 | Simon ........................ 128/1 R |
| 4,723,549 A | | 2/1988 | Wholey et al. |
| 4,997,435 A | | 3/1991 | Demeter |
| 5,100,425 A | | 3/1992 | Fischell et al. |
| 5,158,548 A | | 10/1992 | Lau et al. |
| 5,437,632 A | | 8/1995 | Engleson |
| 5,814,064 A | | 9/1998 | Daniel et al. |
| 5,827,324 A | | 10/1998 | Cassell et al. |
| 5,846,251 A | | 12/1998 | Hart |
| 5,911,734 A | | 6/1999 | Tsugita et al. |
| 5,941,896 A | * | 8/1999 | Kerr ........................... 606/200 |
| 5,980,555 A | | 11/1999 | Barbut et al. |
| 5,989,281 A | | 11/1999 | Barbut et al. |
| 6,168,579 B1 | * | 1/2001 | Tsugita ........................ 606/200 |
| 6,171,328 B1 | * | 1/2001 | Addis .......................... 606/200 |
| 6,179,859 B1 | * | 1/2001 | Bates et al. .................. 606/200 |

FOREIGN PATENT DOCUMENTS

| | | |
|---|---|---|
| WO | WO 99/23976 | 5/1999 |
| WO | WO 99/44510 | 9/1999 |

* cited by examiner

*Primary Examiner*—Eduardo C. Robert
(74) *Attorney, Agent, or Firm*—Fulwider Patton Lee & Utecht, LLP (57) ABSTRACT

A system used in a blood vessel when an interventional procedure is being performed in a stenosed or occluded region to capture any embolic material which may be created and released into the bloodstream during the procedure. The system includes filtering elements which are capable of occluding a blood vessel distal to an interventional procedure site, while enabling the blood to flow past the occlusion and filtering the blood to capture embolic material which may be released into the blood during a therapeutic interventional procedure. The filtering elements include an expandable member which is capable of being expanded distal to the area of treatment at the interventional procedure site for occluding the blood vessel and for enabling the blood to pass therethrough while preventing emboli from passing therethrough. The system also includes a sheath movable distally and proximally to enable the filtering elements to expand into position distal to the interventional procedure site for capturing embolic material and to collapse the filtering elements to retain the captured embolic material therein.

30 Claims, 7 Drawing Sheets

EMBOLIC PROTECTION SYSTEM AND METHOD INCLUDING FILTERING ELEMENTS

BACKGROUND OF THE INVENTION

The present invention relates generally to a system which can be used when an interventional procedure is being performed in a stenosed or occluded region of a blood vessel to capture any embolic material that may be created and released into the bloodstream during the procedure. The system of the present invention is particularly useful when performing balloon angioplasty, stenting procedures, laser angioplasty or atherectomy in critical vessels, such as the carotid arteries, where the release of embolic debris into the bloodstream can occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment or blood vessel or other arterial lumen. Stents are particularly useful in the treatment of repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanum (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and enter the bloodstream. Likewise, emboli may enter the bloodstream as well.

When any of the above-described procedures are performed in the carotid arteries, the release of emboli into the circulatory system can be extremely dangerous to the patient. Debris that is carried by the bloodstream to distal vessels of the brain can cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of a filter or trap downstream from the treatment site to capture embolic debris before it reaches the smaller blood vessels downstream. However, there have been problems associated with filtering systems, particularly during the expansion and collapsing of the filter within the body vessel. If the filtering device does not have a suitable mechanism for closing the filter, there is a possibility that trapped embolic debris can backflow through the open end of the filter and enter the bloodstream as the filtering system is being collapsed for removal from the patient. In such a case, the act of collapsing the filter device may actually squeeze trapped embolic material through the opening of the filter. The need for existing filters to be deployed in the full flow stream of the vessel without alternative paths for embolus free blood to supply the brain may result in deformation or incomplete deployment of the filter. In other instances, the rate of blood percolating through the filtering material may be slower than the normal blood flow which can either result in inadequate blood flow or promote clogging of the filter. If a filter should become clogged when in use in the carotid arteries, blood flow could be diminished to the vessels leading to the brain. While the brain may be capable of functioning for a very short period of time without sufficient blood flow, blood stoppage of more than thirty to forty seconds could cause the patient to experience a seizure or transient ischemic attacks. If the physician administering the procedure is unaware that the filtering device is clogged and that there is little or no blood flowing to the brain, the injury to the patient can be as devastating as if an emboli itself had caused blockage of the cerebral arteries.

What has been needed is a reliable system and method for treating stenosis in blood vessels which prevent the risk of releasing embolic debris into the bloodstream that can cause blockage in vessels at downstream locations. The system and method should be capable of filtering any embolic debris which may be released into the bloodstream during the treatment, and yet allow a sufficient amount of oxygenated blood to flow past the filtering device to supply vital organs downstream from the treatment site. The system and method should be relatively easy for a physician to use and should provide a failsafe filtering system which removes all embolic debris from the bloodstream. Moreover, such a system should be relatively easy to deploy and remove from the patient's vasculature. The inventions disclosed herein satisfy all of these needs.

SUMMARY OF INVENTION

The present invention provides a system and method for capturing embolic debris in a blood vessel which may be created during the performance of a therapeutic interventional procedure, such as a balloon angioplasty or stenting procedure, in order to prevent the embolic debris from lodging and blocking blood vessels downstream from the interventional site. The present invention is particularly useful while performing an interventional procedure in vital arteries, such as the carotid arteries, in which critical downstream blood vessels can become blocked with embolic debris, including the main blood vessels leading to the brain or other vital organs. As a result, the present invention provides the physician with a higher degree of confidence that any and all embolic debris is being collected and removed from the blood vessel when performing high-risk interventional procedures.

The present invention occludes the blood vessel at a location distal to or at the area of treatment in the interventional procedure site, perfuses the blood to enable blood to flow past the occlusion, and filters the blood to capture any embolic debris which may be created during the interventional procedure.

In the present invention, the system includes a filter including filtering elements to occlude a blood vessel and to capture and retain embolic material. The emboli-capturing system of the present invention directs the blood flow through the area where the interventional procedure is to be performed and through the filtering elements located distal to the interventional site, which are designed to capture any friable plaque deposits. Additionally, the present invention allows blood to flow past the filtering elements to provide a continuous stream of blood to the organs located downstream.

In an embodiment of the present invention, the embolic protection system includes a shaft which has a proximal and distal end, and which is adapted to extend distal to the interventional procedure site. A filter including filtering elements is adapted to be located in the distal end portion of the shaft. The filtering elements are adapted to be expandable, and can be deployed within the blood vessel to prevent blood flow past the expandable member, for occluding the blood vessel at a location distal to the interventional procedure site. The expandable filtering elements are further adapted to enable blood to flow therethrough. As a result, even though the expandable filtering elements occlude the blood vessel, the blood will continue to flow past the expandable filtering elements. The blood flowing into and through the filtering elements distal of the interventional site enables the filtering elements to capture embolic material which may be released into the blood in the blood vessel during the interventional procedure. The system further includes a sheath for enabling the filtering elements to expand and contract upon movement of the sheath proximally and distally relative to the filtering elements. The sheath may be located proximal or distal of the filtering elements. The filtering elements are further adapted to be collapsible upon movement of the sheath relative to the filtering elements to retain embolic material captured therein.

The sheath and the shaft of the emboli-capturing system, once deployed within the patient's vasculature, can be used as a guidewire to allow interventional instruments to be moved along the sheath and the shaft into the area of treatment in an over-the-wire arrangement. This eliminates the need to maintain a separate guidewire in the patient once the sheath and the shaft are in place.

In one particular embodiment of the embolic protection system of the present invention, the filtering elements include a plurality of bristles extending from a distal section of the shaft, and a net located distal of the bristles. The sheath may be movable distally to enable the net and the bristles to expand, and proximally to collapse the net and the bristles to retain captured embolic material. In another particular embodiment, the filtering elements comprise a basket, and the sheath is movable distally to enable the basket to expand, and proximally to collapse the basket. In a further embodiment of the invention, the filtering elements comprise a net in a distal section of the shaft, and a serf-expanding stent located proximal of the net. The sheath is movable proximally to release the net and the stent, and is movable distally to contract the net to retain the embolic material captured therein.

Other features and advantages of the present invention will become more apparent from the following detailed description of the preferred embodiments of the invention, when taken in conjunction with the accompanying exemplary drawings.

DETAILED DESCRIPTION OF THE PREFERRED EMBODIMENTS

The present invention is directed to an improved system and method for efficiently and effectively capturing embolic debris which may be released into the bloodstream when performing an interventional procedure in a blood vessel. The preferred embodiments of the improved system and method are illustrated and described herein by way of example only and not by way of limitation. While the present invention is described in detail as applied to the carotid arteries of the patient, and the disclosed interventional procedure is directed to a stenting procedure, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as balloon angioplasty, laser angioplasty or atherectomy.

Referring now to the drawings, wherein like reference numerals denote like or corresponding parts throughout the drawing figures, and particularly to FIGS. 1–9, an embolic protection system 10 is provided for capturing embolic material 12 which may be released into the blood in a blood vessel 14 during a therapeutic interventional procedure. The emtbolic protection system 10 is adapted to capture embolic material 12 which may be released into the blood in the blood vessel 14 during the interventional procedure. Additional details regarding the particular structure and shape of the various elements making up the embolic protection system 10 are provided below.

Figure 1:
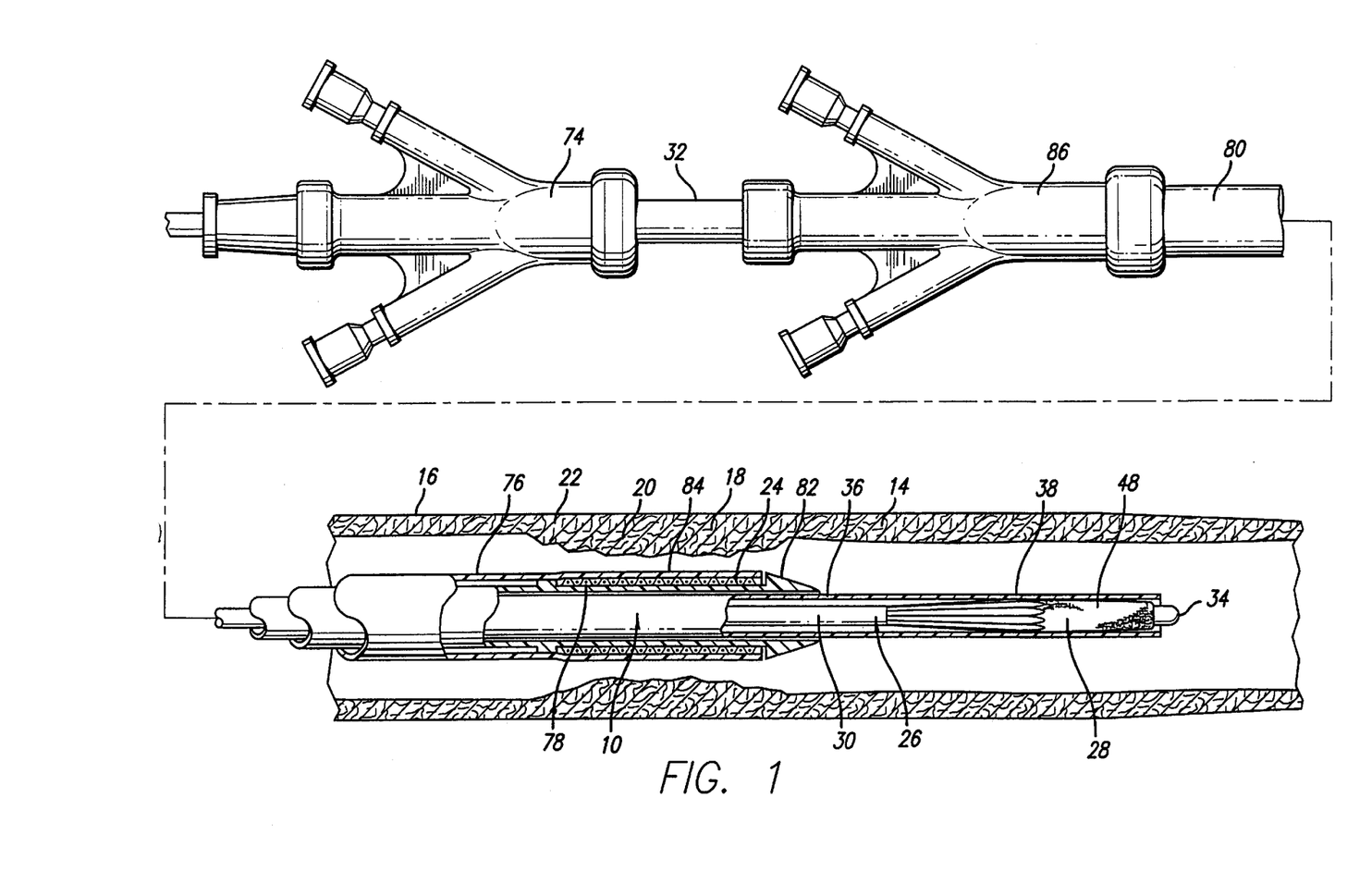
FIG. 1 is an elevational view, partially in section, depicting the embolic protection system of the present invention disposed within the internal carotid artery of the patient, in a first embodiment of the filtering elements for capturing embolic material with a sheath covering the filtering elements.
Figure 2:
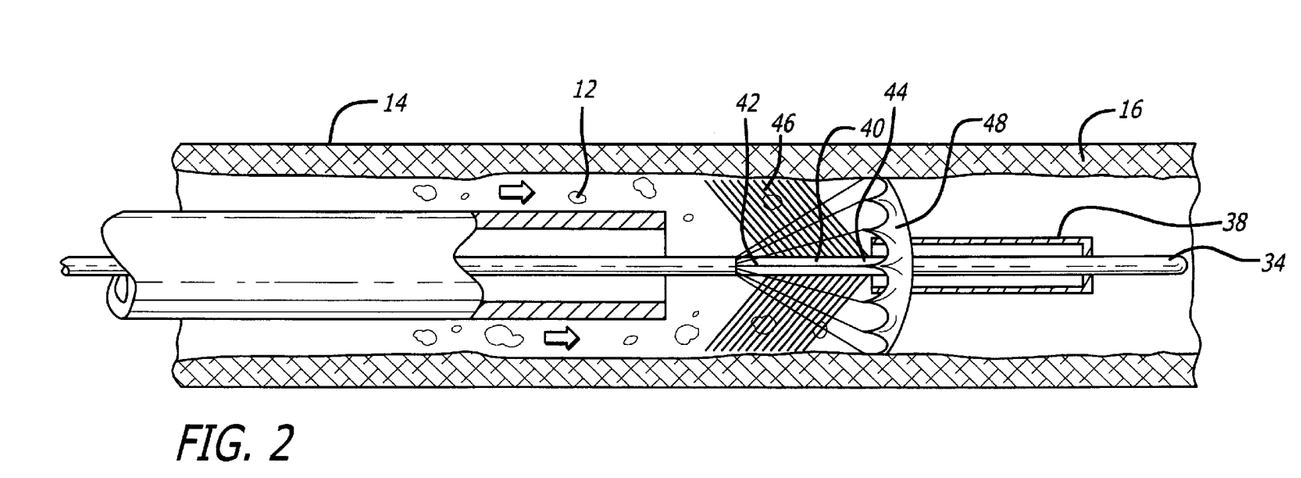
FIG. 2 is an elevational view, partially in section, in a first version of a first mode of the first embodiment of the filtering elements with a sheath retracted from covering a filtering element.
Figure 2A:
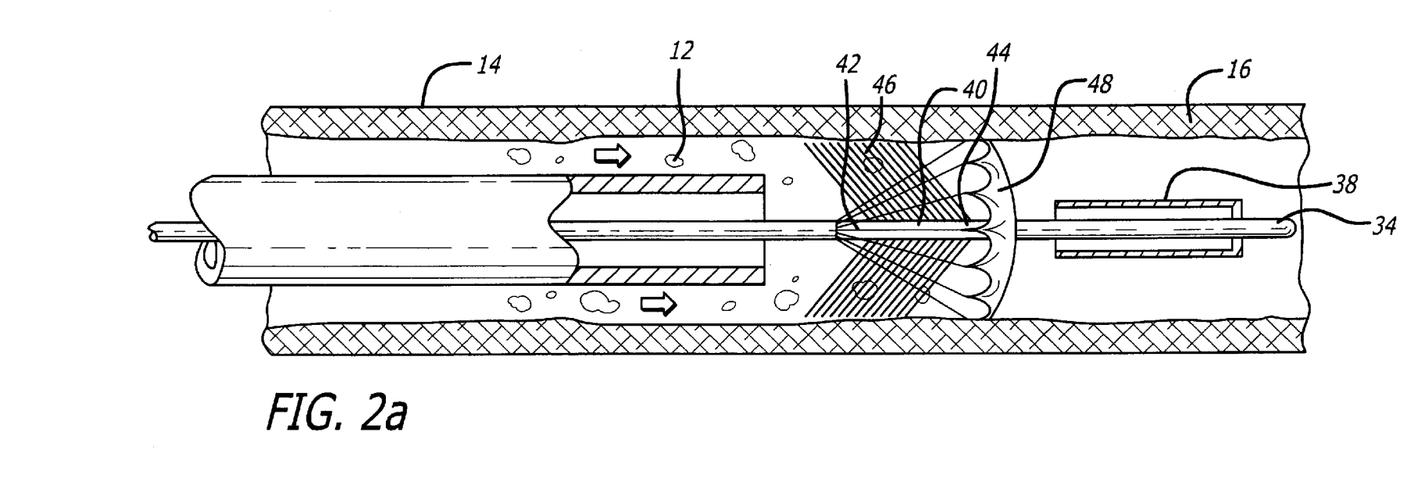
FIG. 2a is an elevational view, partially in section, in a second version of a first mode of the first embodiment of the filtering elements with a sheath retracted from covering a filtering element.
Figure 3:
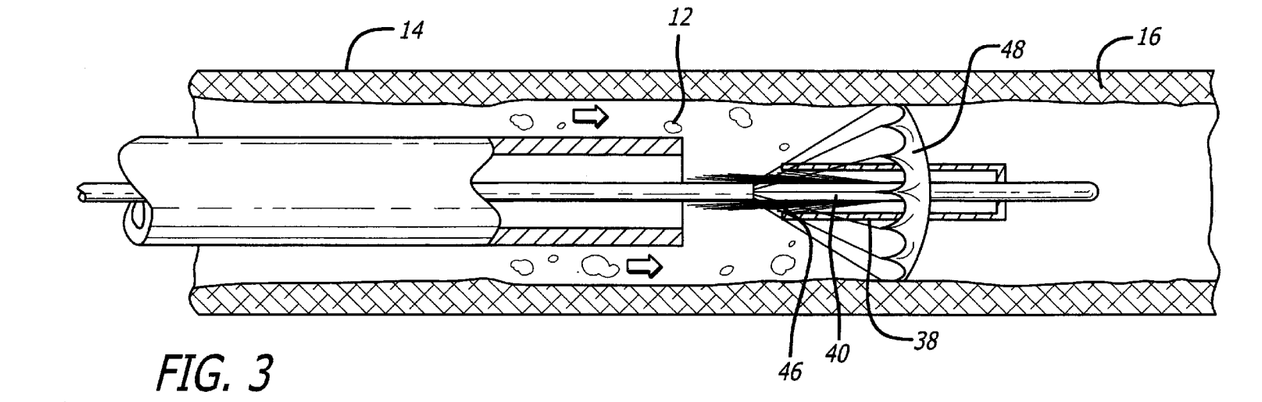
FIG. 3 is an elevational fragmentary view, partially in section, similar to that shown in FIG. 2, of the first version of the first mode of the first embodiment of the filtering elements with a sheath covering a filtering element.
Figure 3A:
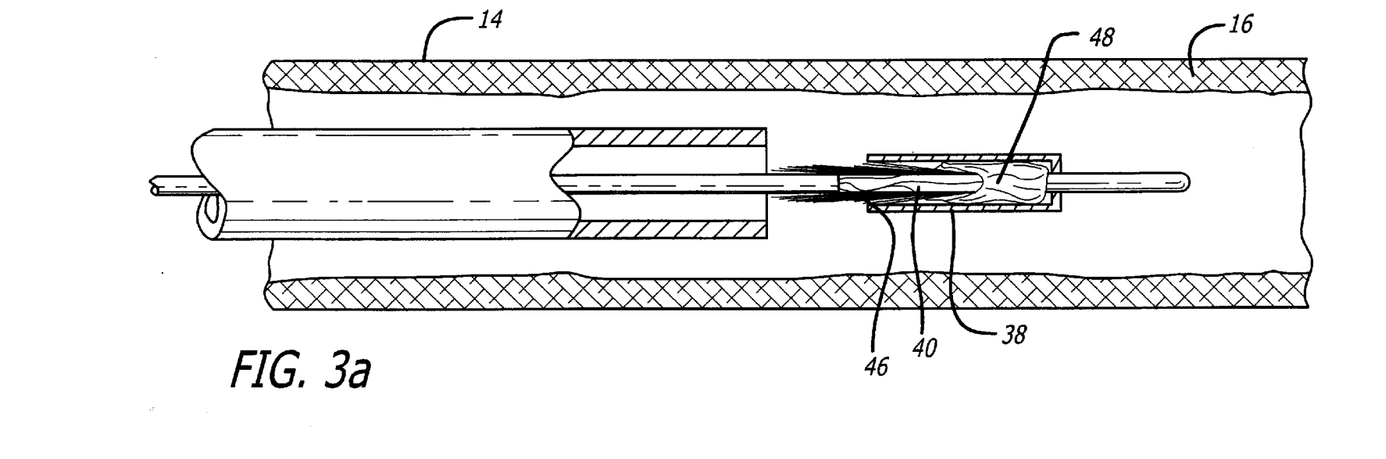
FIG. 3a is an elevational fragmentary view, partially in section, similar to that shown in FIG. 2a, of the second version of the first mode of the first embodiment of the filtering elements with a sheath covering a filtering element.

The embolic protection system 10 as shown in FIG. 1 may be placed within the carotid artery 16 or other blood vessel of the patient. The carotid artery 16 may have an area of treatment 18 wherein atherosclerotic plaque 20 has built up against the inside wall 22 which decreases the diameter of the carotid artery 16. As a result, blood flow may be diminished through this area. As will be discussed below, the therapeutic interventional procedure may comprise implanting a self-expanding expanding stent 24 in the area of treatment 18, to compress the build-up of plaque 20 of the stenosis against the inside wall 22, to increase the diameter of the treatment area 18 of the artery 16, and to help restore sufficient flow of blood to the downstream vessels leading to the brain. The self-expanding stent 24 not only helps increase the diameter of the treatment area, but may help prevent restenosis therein.

The embolic protection systems 10 includes a filter 26, which includes elements 28 for filtering embolic material 12. The filtering elements 28 are adapted to be deployed distal to the area of treatment 18, to enable blood to pass therethrough, and to capture and retain embolic material 12 which may be released into the blood in the blood vessel 14 during the interventional procedure. The filtering elements 28 are further adapted to be expandable to capture embolic material 12, and to be collapsible to retain the captured embolic material 12.

The embolic protection system 10 further includes a shaft 30, adapted to be positionable within the blood vessel 14 and distal to the area of treatment 18. The shaft 30 includes a proximal end 32 and a distal end 34: The shaft 30 may comprise a guide wire 35.

The embolic protection system 10 also includes an element 36 adapted to be movable so as to enable the filtering elements 28 to expand and contract. The expansion enabling element 36 may comprise a sheath 38, adapted to retract from the filtering elements 28 so as to enable the filtering elements 28 to expand to capture embolic material 12 therein, and adapted to project over the filtering elements 28 so as to enable the filtering elements 28 to contract to retain captured embolic material 12 therein.

Figures 4, 5:
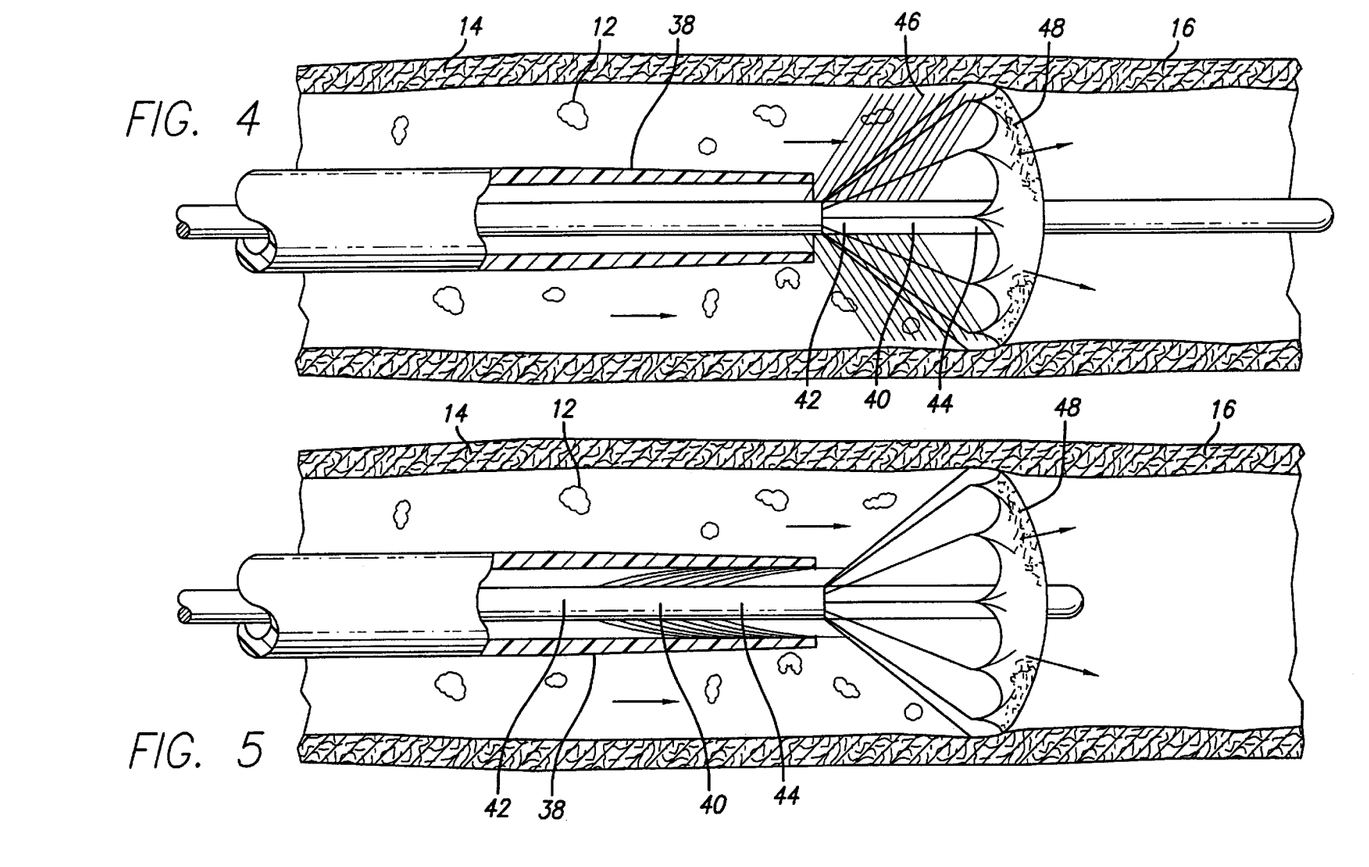
FIG. 4 is an elevational view, partially in section, in a second mode of the first embodiment of the filtering elements with a sheath retracted from covering a filtering element.
FIG. 5 is an elevational view, partly in section, similar to that shown in FIG. 4, of the second mode of the first embodiment of the filtering elements with the sheath covering a filtering element.
Figures 6, 7:
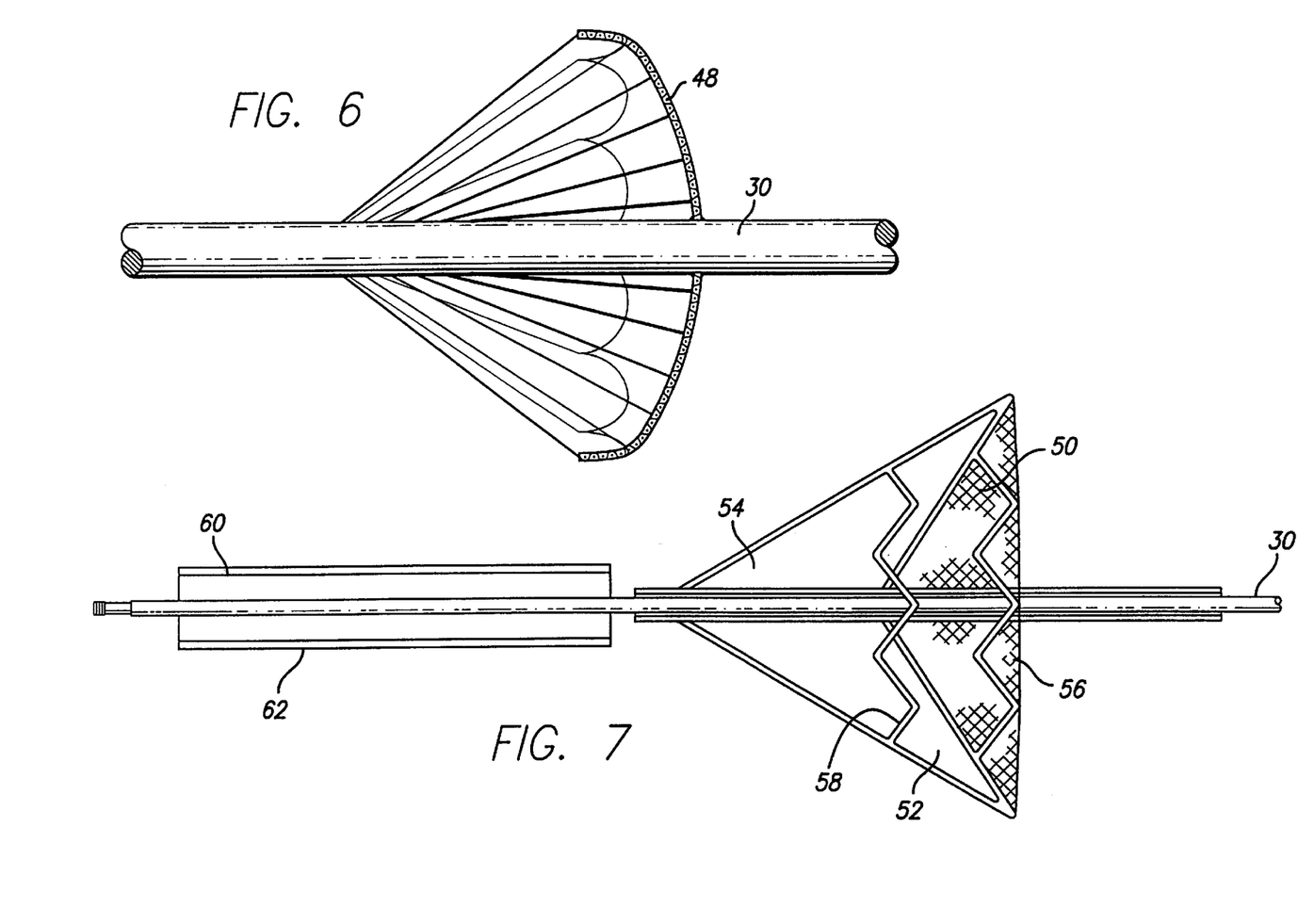
FIG. 6 is an elevational fragmentary view, partly in section, of a filtering element in the first embodiment of the present invention.
FIG. 7 is an elevational view, partially insection, of a second embodiment of the filtering elements in the embolic protection system of the invention.
Figure 8:
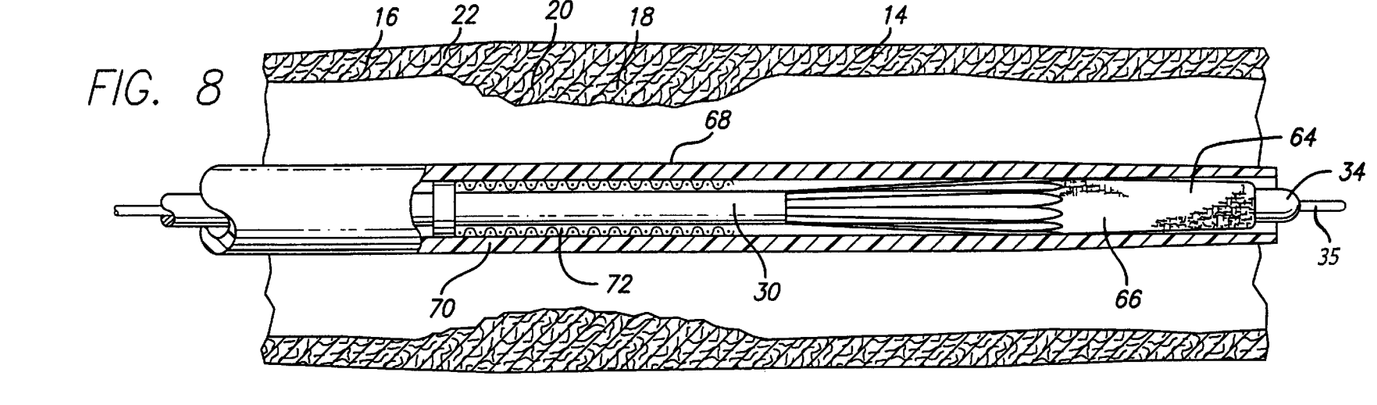
FIG. 8 is an elevational view, partially in section, of a third embodiment of filtering elements in the embolic protection system of the present invention, with a sheath covering a filtering element and a stent.
Figure 9:
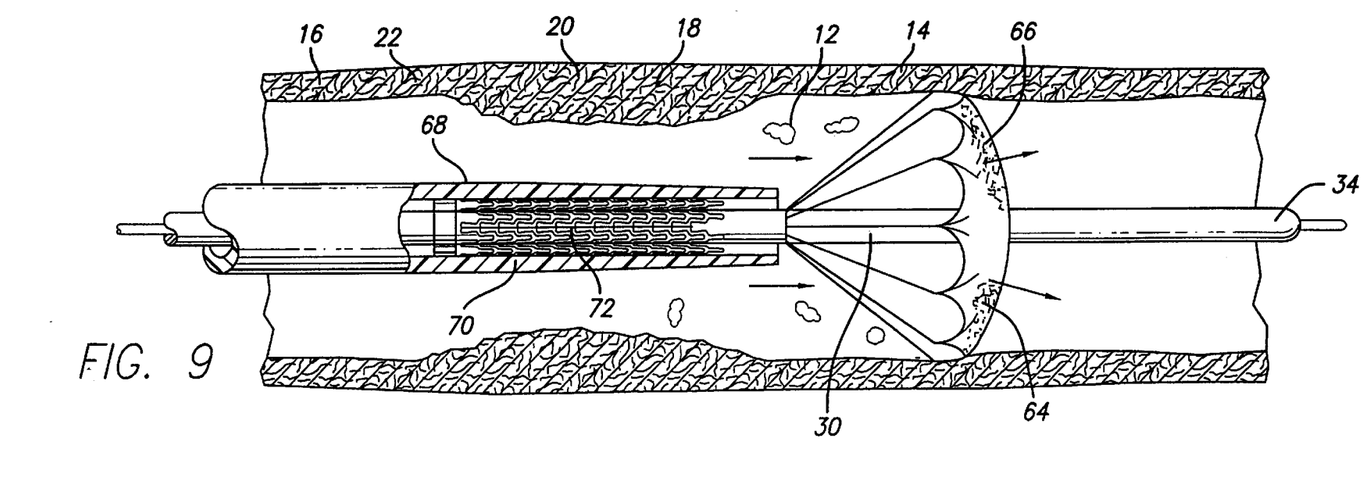
FIG. 9 is an elevational view, partially in section, similar to that shown in FIG. 6, in the third embodiment of the invention with the sheath retracted from covering the filtering element.
Figure 10:
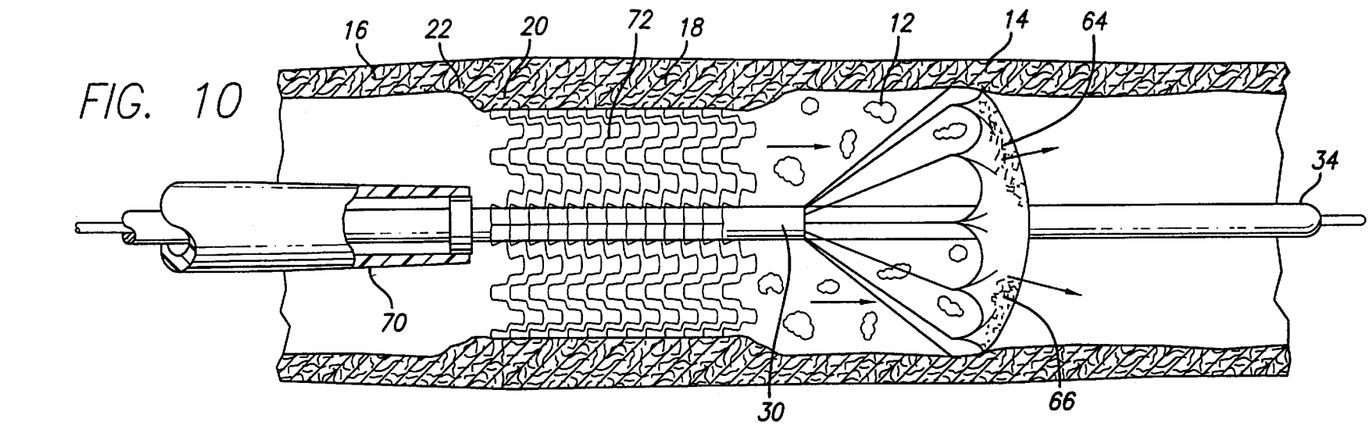
FIG. 10 is an elevational view, partially in section, in the third embodiment of the invention with the sheath uncovering the stent.
Figure 11:
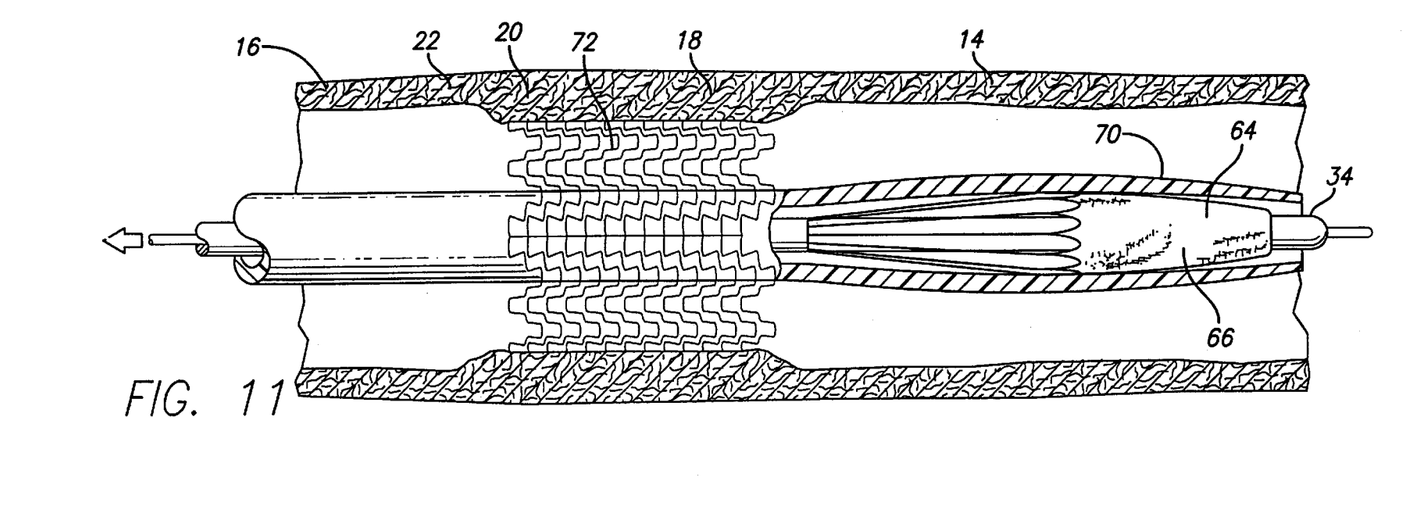
FIG. 11 is an elevational view, partially in section, in the third embodiment of the invention with the sheath covering the filtering element.

As shown in a first embodiment in FIGS. 1–6, the shaft 30 may further include a section 40 in the distal end portion 34 of the shaft 30, where one of the filtering elements 28 may be located. The shaft section 40 includes a proximal end 42 and a distal end 44. Further in such embodiment, the filtering elements 28 may include a plurality of bristles 46, extending from the shaft section 40, adapted to capture embolic material 12. As shown in FIGS. 1, 2, 3, 2a, and 3a in a first mode of the first embodiment, the bristles 46 may extend from the shaft section 40 in a direction which is generally the opposite of the direction of flow of the blood in the blood vessel 14. In such mode, the sheath 38 may be movable proximally to cover the bristles 46 and distally to enable the bristles 46 to expand. As shown in FIGS. 4–6 in a second mode of the first embodiment, the bristles 46 may extend from the shaft section 40 in a direction which is generally the same as the direction of flow of the blood in the blood vessel 14. In such mode, the sheath 38 may be movable distally to cover the bristles 46, and may be movable proximally to enable the bristles 46 to expand. In both such modes, when the sheath 38 covers the bristles 46, it is adapted to fold the bristles 46 down over each other to retain captured embolic material 12 therein. The bristles 46 may be spaced apart a distance generally less than the smallest dimension of the embolic material 12 to be captured thereby. The bristles 46 may also be spaced apart a distance which varies from the proximal end 42 to the distal end 44 of the shaft section 40 to capture embolic material 12 of different sizes. The filtering elements 28 may further include a net 48 located distal of the bristles 46, and adapted to be deployed to capture embolic material 12.

As shown in FIG. 7, alternatively, the filtering elements 28 may comprise a filtering element 50 which may comprise, for example, a basket 52, mounted on the shaft 30. The basket 52 includes a distal end 54 which is open, and a proximal end 56 secured to the shaft 30. The basket 52 includes wire ribs 58 extending about the periphery thereof. The expansion enabling element 36 may comprise an expansion enabling element 60 for enabling the basket 52 to expand and contract, adapted to be located distal of the basket 52, movable distally to enable the basket 52 to expand, and movable proximally to cover the basket 52 and to enable the basket 52 to contract. The expansion enabling element 60 may comprise a sheath 62, adapted to be movable proximally so as to extend over the basket 52 to enclose the basket 52 and retain embolic material 12 captured in the basket 52. The sheath 62 may be generally tubular-shaped or ring-shaped.

As seen in FIGS. 8–11, alternatively, the filtering elements 28 may comprise a filtering element 64, which may comprise a net 66, adapted to be deployed to capture embolic material 12. The expansion element 36 may comprise an expansion enabling element 68 for enabling the net 66 to expand and contract, adapted to be located proximal of the net 66, movable distally to cover the net 66 and to enable the net 66 to contract, and movable proximally to enable the net 66 to expand. The expansion enabling element 68 may comprise a sheath 70, adapted to be movable distally to extend over the net 66 and to enclose and retain embolic material 12 captured in the net 66. The system 10 in such embodiment may further include an interventional instrument adapted to be deployed at the interventional procedure site, comprising a self-expanding stent 72, adapted to be releasably mounted on the shaft 30 proximal of the net 66 and enclosed in the sheath 70, and adapted to be released upon movement proximally of the sheath 70 to enable the stent 74 to expand.

As shown in FIG. 1, the embolic-protection system 10 may further include a multi-arm adapter 74 attached to the proximal end 32 of the shaft 30. The embolic protection system 10 may further comprise an interventional instrument catheter 76, adapted to be movable along the emboli-capturing catheter 16 so as to pass interventional instruments such as the self-expanding stent 24 to the interventional procedure site at the area of treatment 18. The interventional instrument catheter 76 includes an elongated shaft 78 which includes a proximal end 80 and a distal end 82 for delivering the interventional instruments (herein the stent 24 located near the distal end 82 of the elongated shaft 78) into the area of treatment 18. The interventional instrument catheter 76 may also include a retractable sheath 84 for covering the self-expanding stent 24 until it is positioned at the treatment area 18, and for being retracted so as to release the self-expanding stent 24 at the treatment area 18. The interventional instrument catheter 76 may further include a multi-arm adapter 86, such as a Tuohy-Borst adapter, attached to a proximal end 80 of the elongated shaft 30.

In use, as illustrated in FIGS. 1–6, the embolic protection system 10 may be positioned in the patient's vasculature utilizing any one of a number of different methods. In one preferred method of positioning, the embolic-protection system 10 may be placed in the blood vessel 14 by utilizing the shaft 30 which is inserted into the patient's vasculature and manipulated by the physician to the area of treatment 18.

In the embodiment of FIGS. 1–6, as shown in FIG. 1, once the shaft 30 is in position in the blood vessel 14 with the net 48 and the bristles 46 distal to the treatment area 18, the sheath 38 may be moved proximally to enable the net 48 and the bristles 46 to expand distal to the treatment area 18 so as to enable blood to flow therethough and to capture embolic material 12.

In the embodiment of the invention illustrated in FIGS. 1–6, as seen in FIG. 1, once the system 10 is placed in the patient's vasculature, with the net 48 and the bristles 46 positioned distal to the treatment area 18, an interventional device, such as the interventional instrument catheter 76 including the a self-expanding stent 24, may be positioned in the area of treatment 18 utilizing the sheath 38 of the embolic-protection system 10 as a guidewire, using well-known over-the-wire techniques. Upon positioning the self-expanding stent 24 at the treatment area 18, the retractable sheath 84 of the interventional instrument catheter 76 may be retracted through use of the adapter 86, releasing the self-expanding stent 24 to compress the build-up of plaque 20 in the treatment area 18. Any embolic material 12 which may be released into the blood during the therapeutic procedure may then be directed with the blood flow through the bristles 46 and the net 48 for filtering thereof, to capture embolic material 12 which may be released into the blood in the blood vessel 14 during the interventional procedure. The bristles 46 are adapted to capture generally larger embolic material 12 as a pre-filter to prevent the generally larger embolic material 12 from clogging the net 48, and, in cooperation with the net 48, to prevent embolic material 12 from passing therethrough with the blood, for filtering embolic material 12. Then, after a sufficient time passes to allow any embolic material 12 released into the blood to be captured by the bristles 46 and the net 48, the sheath 38 may be moved distally to collapse the bristles 46 and the net 48 so as to retain the captured embolic material 12 therein, and the interventional instrument catheter 76 along with embolic material 12 captured in the bristles 46 and the net 48 may be withdrawn from the blood vessel 14, leaving the stent 24 in position therein.

In the embodiment of the invention illustrated in FIG. 7, once the embolic protection system 10 is in place in the patient's vasculature 14 the sheath 62 may be moved distally to enable the basket 52 to expand at a location distal to the area of treatment 18. The expanded basket 52 enables blood to flow therethrough and captures embolic material 12 therein. The self-expanding stent 24 may then be positioned and deployed, as set forth above. The expanded basket 52 may then capture embolic material 12 released into the blood in the blood vessel 14 upon deployment of the stent 24. After the stent 24 is deployed in the treatment area 18, the interventional instrument catheter 76 may be withdrawn. Then, after a sufficient time to allow embolic material 12 released into the blood in the blood vessel 14 to be captured by the expanded basket 52, the sheath 62 may be moved proximally to collapse the basket 52 and retain therein the captured embolic material 12, and the intervention instrument catheter 76 and the basket 52 may be withdrawn from the blood vessel 14, leaving the stent 24 in position therein.

In the embodiment as shown in FIGS. 8–11, after placement of the embolic protection system 10 in the patient's blood vessel 14, with the net 66 located distal of the treatment area 18 and the stent 72 located at the treatment area 18, the sheath 70 may be moved proximally to enable the net 66 to expand, for enabling blood to flow therethrough and for capturing embolic material 12 therein. Upon further proximal movement of the sheath 70, the self-expanding stent 72 is released to compress the build-up of the plaque 20 in the area of treatment 18. Embolic material 12 released into the blood during the therapeutic procedure may then be directed with the blood flow through the net 66 to capture embolic material 12 for filtering thereof The sheath 70 may then be moved distally to collapse the net 66 for retaining captured embolic material 12 therein. The shaft 30 and the net 66 may then be withdrawn from the blood vessel 14, leaving the stent 72 in position therein.

It should be appreciated that the particular embodiments of the filtering elements 28 are capable of being positioned in the blood vessel 14. However, other forms of filtering elements 28 may be utilized with the present invention without departing from the spirit and scope of the invention. For example, filtering elements 28 may further be comprised of other forms of material. Additionally, while the filtering elements 28 are shown as in various shapes in the embodiments herein, they can be formed in any one of a number of different shapes depending upon the construction desired.

The embolic protection system 10 of the present invention may be formed of conventional materials of construction. The filtering elements 28 can be made out of relatively inelastic materials such as polyethylene, polyvinyl chloride, polyesters and composite materials such as polyurethanes. The bristles 46 can be added by molding, glueing, bonding, or mechanically constraining the bristles between twisted, coiled, or braided wire that makes up the shaft, or by adding a separator that forms the bristles, formed as a sleeve over the shaft. The various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed.

In view of the foregoing, it is apparent that the system and method of the present invention enhances substantially the safety of performing interventional procedures by significantly reducing the risks associated with embolic material being created and released into the patient's bloodstream. Further modifications and improvements may additionally be made to the system and method disclosed herein without the departing from the scope of the invention. Accordingly, it is not intended that the invention be limited, except as by the appended claims.

What is claimed is:

1. A system for capturing embolic material which may be released into a blood vessel during a therapeutic interventional procedure, comprising:
    a shaft, adapted to be positionable within the blood vessel and distal to an interventional procedure site, wherein the shaft has proximal and distal ends; and
    a filter, adapted to be located in a distal end portion of the shaft, to be deployed distal to the interventional procedure site, and to pass blood therethrough and to capture embolic material which may be released into the blood in the blood vessel during the interventional procedure, wherein the filter includes elements for filtering embolic material, adapted to be expandable to capture embolic material, and to be collapsible to retain the captured embolic material, and wherein the filtering elements include a plurality of bristles permanently attached and extending from a section of the distal end portion of the shaft, and adapted to capture embolic material.

2. The system of claim 1, wherein the filtering elements further include a net located distal of the plurality of bristles and adapted to be deployed to capture embolic material.

3. The system of claim 1, wherein the shaft comprises a guide wire.

4. The system of claim 1 further comprising an interventional instrument catheter adapted to be movable along the shaft so as to pass an interventional instrument to the interventional procedure site.

5. The system of claim 1, further comprising an expansion and contraction enabling element for enabling the filtering elements to expand and contract, adapted to be movable proximally to enable the filtering elements to expand, and movable distally to cover the filtering elements and enable the filtering elements to contract.

6. The system of claim 5, wherein the expansion and contraction enabling element comprise a sheath adapted to extend over the bristles so as to fold the bristles down over each other and retain the embolic material captured on the bristles.

7. The system of claim 5, further comprising an interventional instrument adapted to be deployed at the interventional procedure site, comprising a self-expanding stent adapted to be releasably mounted on the shaft proximal of the filter and enclosed in the expansion and contraction enabling element, wherein the expansion and contraction enabling element is further adapted upon movement proximally to enable the self-expanding stent to expand.

8. The system of claim 7, wherein the filtering elements comprise a net, located distal of the self-expanding stent and adapted to be deployed to capture embolic material.

9. The system of claim 1, further comprising an expansion and contraction enabling element for enabling the filtering elements to expand and contract, adapted to be movable distally to enable the filtering elements to expand, and movable proximally to cover the filtering elements and enable the filtering elements to contract.

10. The system of claim 1, wherein the blood flows in a blood flow direction in the blood vessel, and the bristles extend from the shaft in a direction which is generally the opposite of the blood flow direction.

11. The system of claim 1, wherein the bristles extend from the shaft in a direction which is generally the same as the direction of the flow of the blood in the blood vessel.

12. The system of claim 1, wherein the embolic material to be captured thereby include a smallest dimension, and the bristles are spaced apart a distance generally less than the smallest dimension.

13. The system of claim 1, wherein the bristles are spaced apart a distance which varies from the proximal to the distal end of the shaft section to capture embolic material of different sizes.

14. The system of claim 1, wherein the filtering elements further include a net located distal of the plurality of bristles and adapted to be deployed to capture generally small embolic material.

15. The system of claim 1, wherein the bristles are spaced apart a distance generally less than a smallest dimension of the embolic material to be captured thereby.

16. A method of capturing embolic material which may be released into a blood vessel during a therapeutic interventional procedure, in a system which comprises a shaft, adapted to be positionable within the blood vessel and distal to an interventional procedure site, wherein the shaft has proximal and distal ends, and a filter, adapted to be located in a distal end portion of the shaft, to be deployed distal to the interventional procedure site, and to pass blood therethrough and to capture embolic material which may be released into the blood in the blood vessel during the interventional procedure, wherein the filter includes elements for filtering embolic material, adapted to be expandable to capture embolic material, and to be collapsible to retain the captured embolic material, wherein the filtering elements include a plurality bristles permanently attached and extending from a section of the distal end portion of the shaft, and adapted to capture embolic material, wherein the method comprises:

positioning the shaft in the interventional procedure site such that the filter is located within the blood vessel in the region at a location distal to the interventional procedure site;

expanding the plurality of bristles within the blood vessel at the location distal to the interventional procedure site so as to enable the capture of embolic material;

performing the interventional procedure, which may release embolic material into the blood;

filtering the blood through the plurality of bristles so as to capture embolic material which may be released into the blood upon performing the interventional procedure; and     collapsing the filtering elements so as to retain the captured embolic material.

17. The method of claim 16, wherein the filtering elements further include a net located distal of the bristles and adapted to be deployed to capture embolic material, and wherein filtering further comprises filtering the blood through the net to capture embolic material.

18. A system for capturing embolic material which may be released into a blood vessel during a therapeutic interventional procedure, comprising:

a shaft, adapted to be positionable within the blood vessel and distal to an interventional procedure site, wherein the shaft has proximal and distal ends; and     a filter, adapted to be located in a distal end portion of the shaft, to be deployed distal to the interventional procedure site, and to pass blood therethrough and to capture embolic material which may be released into the blood in the blood vessel during the interventional procedure, wherein the filter includes elements for filtering embolic material, adapted to be expandable to capture embolic material, and to be collapsible to retain the captured embolic material, wherein the filtering elements include a plurality of bristles, extending from a section of the distal end portion of the shaft, and adapted to capture embolic material, and wherein the filtering elements further include a net located distal of the plurality of bristles and adapted to be deployed to capture embolic material.

19. The system of claim 18, wherein the blood flows in a blood flow direction in the blood vessel, and the bristles extend from the shaft in a direction which is generally the opposite of the blood flow direction.

20. The system of claim 18, wherein the shaft section includes proximal and distal ends, and the bristles are spaced apart a distance which varies from the proximal to the distal end of the shaft section to capture embolic material of different sizes.

21. A system for capturing embolic material which may be released into a blood vessel during a therapeutic interventional procedure, comprising:

a shaft, adapted to be positionable within the blood vessel and distal to an interventional procedure site, wherein the shaft has proximal and distal ends; and     a filter, adapted to be located in a distal end portion of the shaft, to be deployed distal to the interventional procedure site, and to pass blood therethrough and to capture embolic material which may be released into the blood in the blood vessel during the interventional procedure, wherein the filter includes elements for filtering embolic material, adapted to be expandable to capture embolic material, and to be collapsible to retain the captured embolic material, wherein the filtering elements include a plurality of bristles, extending from a section of the distal end portion of the shaft, and adapted to capture embolic material, wherein the filtering elements further include a net located distal of the bristles and adapted to be deployed to capture generally small embolic material.

22. The system of claim 21, further comprising an interventional instrument catheter adapted to be movable along the shaft so as to pass an interventional instrument to the interventional procedure site.

23. The system of claim 21, further comprising an expansion and contraction enabling element for enabling the filtering elements to expand and contract, adapted to be movable distally to enable the filtering elements to expand, and movable proximally to cover the filtering elements and enable the filtering elements to contract.

24. The system of claim 21, wherein the blood flows in a blood flow direction in the blood vessel, and the bristles extend from the shaft in a direction which is generally the opposite of the blood flow direction.

25. A method of capturing embolic material which may be released into a blood vessel during a therapeutic interventional procedure, in a system which comprises a shaft, adapted to be positionable within the blood vessel and distal to an interventional procedure site, wherein the shaft has proximal and distal ends, and a filter, adapted to be located in a distal end portion of the shaft, to be deployed distal to the interventional procedure site, and to pass blood therethrough and to capture embolic material which may be released into the blood in the blood vessel during the interventional procedure, wherein the filter includes elements for filtering embolic material, adapted to be expandable to capture embolic material, and to be collapsible to retain the captured embolic material, wherein the filtering elements include a plurality of bristles, extending from a section of the distal end portion of the shaft, and adapted to capture embolic material, and wherein the filtering elements further include a net located distal of the bristles and adapted to be deployed to capture embolic material, wherein the method comprises:

positioning the shaft in the interventional procedure site such that the filter is located within the blood vessel in the region at a location distal to the interventional procedure site;

expanding the filtering elements within the blood vessel at the location distal to the interventional procedure site so as to enable the capture of embolic material;

performing the interventional procedure, which may release embolic material into the blood;

filtering the blood through the filtering elements so as to capture embolic material which may be released into the blood upon performing the interventional procedure, further comprising filtering the blood through the bristles to capture embolic material, and filtering the blood through the net to capture embolic material; and collapsing the filtering elements so as to retain the captured embolic material.

26. A method of capturing embolic material which may be released into a blood vessel during a therapeutic interventional procedure, in a system which comprises a shaft, adapted to be positionable within the blood vessel and distal to an interventional procedure site, wherein the shaft has proximal and distal ends, and a filter, adapted to be located in a distal end portion of the shaft, to be deployed distal to the interventional procedure site, and to pass blood therethrough and to capture embolic material which may be released into the blood in the blood vessel during the interventional procedure, wherein the filter includes elements for filtering embolic material, adapted to be expandable to capture embolic material, and to be collapsible to retain the captured embolic material, wherein the filtering elements include a plurality of bristles, extending from a section of the distal end portion of the shaft, and adapted to capture embolic material, wherein the filtering elements further include a net located distal of the bristles and adapted to be deployed to capture generally small embolic material, wherein the method comprises:

positioning the shaft in the interventional procedure site such that the filter is located within the blood vessel in the region at a location distal to the interventional procedure site;

expanding the bristles within the blood vessel at the location distal to the interventional procedure site so as to capture embolic material;

performing the interventional procedure, which may release embolic material into the blood;

filtering the blood through the bristles so as to capture embolic material which may be released into the blood upon performing the interventional procedure, further comprising filtering the blood through the net to capture embolic material; and collapsing the bristles so as to retain the captured embolic material.

27. The method of claim 26, further comprising an interventional instrument catheter adapted to be movable along the shaft so as to pass an interventional instrument to the interventional procedure site, further comprising positioning the interventional procedure catheter at the interventional procedure site.

28. The method of claim 26, further comprising an expansion and contraction enabling element for enabling the filtering elements to expand and contract, adapted to be movable distally to enable the filtering elements to expand, and movable proximally to cover the filtering elements and enable the filtering elements to contract, further comprising moving the expansion and contraction enabling element distally to enable the filtering elements to expand.

29. The method of claim 26, wherein the bristles extend from the shaft in a direction which is generally the opposite of the direction of the flow of the blood in the blood vessel, and wherein expanding further comprises expanding the bristles so that the bristles extend in a direction which is generally opposite the direction of the flow of blood in the blood vessel.

30. The method of claim 26, wherein the shaft section includes proximal and distal ends, and the bristles are spaced apart a distance which varies from the proximal to the distal end of the shaft section to capture embolic material of different sizes, and wherein filtering further comprises filtering the blood through the variably spaced-apart bristles so as to capture embolic material.

* * * * *